(12) United States Patent
Hall

(10) Patent No.: US 7,281,925 B2
(45) Date of Patent: Oct. 16, 2007

(54) IMPLANT ARRANGEMENT

(75) Inventor: Jan Hall, Gothenburg (SE)

(73) Assignee: Nobel Biocare Services AG, Glattbrugg (CH)

( * ) Notice: Subject to any disclaimer, the term of this patent is extended or adjusted under 35 U.S.C. 154(b) by 0 days.

(21) Appl. No.: 11/169,189

(22) Filed: Jun. 28, 2005

(65) Prior Publication Data

US 2006/0003291 A1    Jan. 5, 2006

Related U.S. Application Data

(63) Continuation of application No. PCT/SE03/01973, filed on Dec. 17, 2003.

(30) Foreign Application Priority Data

Dec. 30, 2002    (SE) .................................... 0203896

(51) Int. Cl.
  *A61C 8/00*  (2006.01)
  *A61B 17/86*  (2006.01)
  *F16B 35/04*  (2006.01)
(52) U.S. Cl. .......................... 433/174; 606/73; 411/411
(58) Field of Classification Search ................ 433/174, 433/172, 173, 73, 201.1; 411/411, 413, 308–311, 411/417, 420, 421; 606/73
See application file for complete search history.

(56) References Cited

U.S. PATENT DOCUMENTS

| | | | | |
|---|---|---|---|---|
| 2,215,770 A | * | 9/1940 | Sheffield ................ 285/148.19 |
| 4,103,422 A | | 8/1978 | Weiss et al. |
| 4,863,383 A | * | 9/1989 | Grafelmann ................ 433/174 |
| 4,976,739 A | * | 12/1990 | Duthie, Jr. ................... 606/60 |
| 5,061,181 A | | 10/1991 | Niznick |
| 5,639,237 A | * | 6/1997 | Fontenot ..................... 433/173 |
| 6,129,730 A | | 10/2000 | Bono et al. |
| 6,135,772 A | * | 10/2000 | Jones ........................ 433/174 |
| 6,273,722 B1 | | 8/2001 | Phillips |
| 6,312,259 B1 | * | 11/2001 | Kvarnstrom et al. ........ 433/173 |
| 6,315,564 B1 | * | 11/2001 | Levisman ................... 433/174 |
| 6,419,491 B1 | | 7/2002 | Ricci et al. |
| 6,481,760 B1 | * | 11/2002 | Noel et al. .................. 285/334 |
| 6,726,689 B2 | * | 4/2004 | Jackson ....................... 606/73 |

FOREIGN PATENT DOCUMENTS

WO    WO 03/034951 A1    5/2003

* cited by examiner

*Primary Examiner*—Cary E. O'Connor
(74) *Attorney, Agent, or Firm*—Knobbe Martens Olson & Bear LLP

(57) ABSTRACT

An implant is arranged with a thread which can be exposed to a jaw bone and which has a first extent in the longitudinal direction of the implant. Thread flanks are assigned second extents between the inner and outer peripheries of the thread. Along all or most of the first extent, the thread flanks are arranged with one or more grooves that can extend in the peripheral direction and can be situated on the second extents. The groove or grooves are arranged to participate in the process by which the implant fuses with the jaw bone (2).

39 Claims, 4 Drawing Sheets

A-A

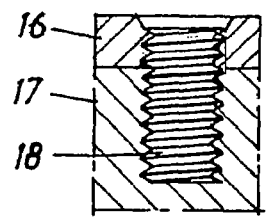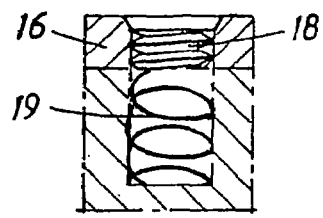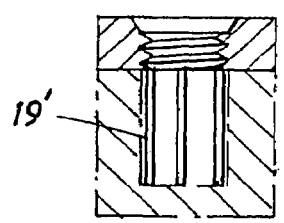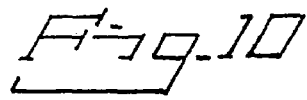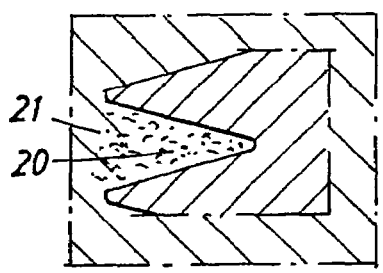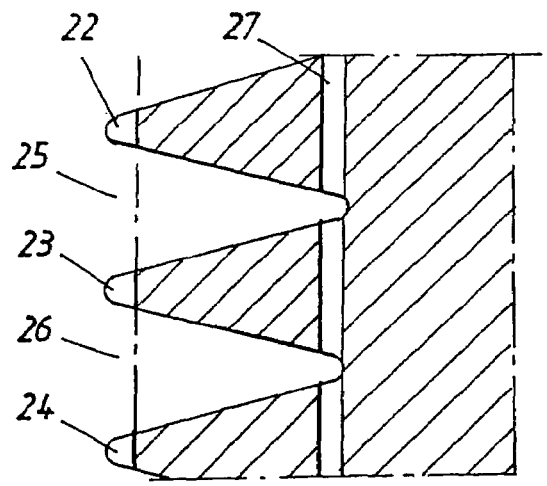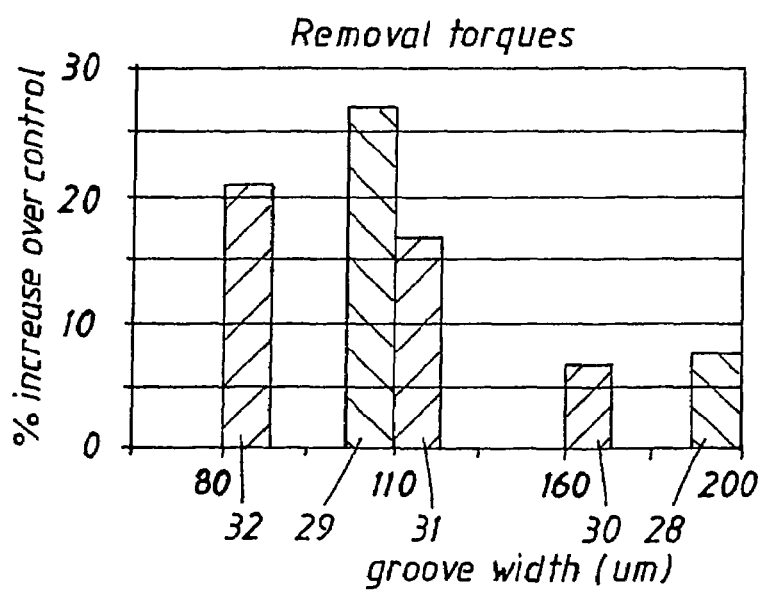

IMPLANT ARRANGEMENT

This application is a continuation of International Application PCT/SE2003/001973, with an international filing date of Dec. 17, 2003, which claims priority under 35 U.S.C. §119 to Swedish Patent Application No. SE 0203896-6, filed Dec. 30, 2002, the entire contents of the international application is expressly incorporated by reference herein.

BACKGROUND OF THE INVENTION

1. Field of the Invention

The present invention relates dental implants, and more particularly, to a dental implant arrangement and methods of manufacturing the same with a thread which can be exposed to a jaw bone and which has a first extent in the longitudinal direction of the implant and in which thread flanks are assigned second extents between the inner and outer peripheries of the thread.

2. Description of the Related Art

In connection with dental implants, there is a need, in different patient situations, to achieve effective functions so as to make the implant fuse in the part of the jaw bone in question. The anchoring of the implant in the jaw bone depends on various factors, for example the part of the jaw bone to be provided with an implant, the patient's condition, etc. Different implant structures, the use of bone-growth-stimulating agents or substances, etc., have been proposed, and in this connection reference may be made inter alia to the patent applications filed by and patents granted to the same Applicant and same inventor as for the present invention. There is, however, a need for further improvements so as to obtain effective fusion and retention of the implant in the jaw bone.

SUMMARY OF THE INVENTION

An object of the present invention is to solve the aforementioned problems and it uses, inter alia, the knowledge that in connection with implants in general, but not implants in dentistry of the type in question here. Thus, it is argued that the degree of anchoring must be able to be stimulated and strengthened by means of recesses having certain widths and depths. This has been shown in cell culture tests, and reference is made inter alia to WO 97/05238. There is also a need to be able to optimize the anchoring or fusion of the implant in the jaw bone and to achieve an effective production of the respective implant or implant type. An object of the invention is to solve this problem too.

Accordingly, an embodiment of the present invention relates to an implant arrangement with a thread which can be exposed to a jaw bone and which has a first extent in the longitudinal direction of the implant and in which thread flanks are assigned second extents between the inner and outer peripheries of the thread. The invention also relates to a method for producing the implant. The implant is to be placed in the upper and lower jaws where the strength of the jaw bone varies and the cortical and trabecular parts or features vary considerably. In soft parts with considerable involvement of trabecular and marrow-filled bone, it is expedient to take measures to increase the anchoring or retention of the implant in this case too. An object of the invention is to also solve this problem.

In accordance with one embodiment of the invention, bone spirals and/or bone strands formed by or with the cortical jaw bone are intended to extend down into the trabecular and marrow-filled parts of the jaw bone. It is important how the spirals and strands are arranged. This embodiment solves this problem too in a technically advantageous manner and permits application of bone-growth-stimulating agents (TS, HA) to the implant in a novel way.

Another embodiment of the present invention comprises, inter alia, that along all or part of the first extent of the implant, the thread flanks are arranged with one or more grooves extending in the peripheral direction and situated on the second extents, i.e., the extents of the thread flanks. In a complementary or alternative configuration, the grooves or recesses are arranged on the inner or outer peripheries of the thread flanks, so that the recesses of thread flanks lying one above the other can be considered to form grooves which extend through the inner or outer edges of the flanks. In the case of the outer edges, the groove or grooves extend via the free spaces between the flanks. The recess arrangement can be such that the strands can be seen to be twisted or straight. In addition, this embodiment is characterized in that the groove or grooves are arranged to participate in the process of fusion or retention of the implant in the jaw bone.

In embodiments of the invention, the groove or grooves of the thread flanks are arranged to increase the surface of the thread flanks exposed to the jaw bone. The groove(s) of the thread flanks can be arranged at the central parts of the thread flanks. The groove depth and/or groove width can be substantially the same or vary along the longitudinal extent of the implant thread. The groove or grooves are situated at the same or varying distance along the various thread flanks. The groove or grooves can be arranged on the upper sides and/or undersides of the thread flanks. In a preferred embodiment, the thread flanks are provided with oxidation layers or porous layers which themselves have a stimulating effect on the anchoring function. In a further alternative embodiment, the thread flanks can be provided with bone-growth-stimulating agent, for example TS, in a gel form or soft consistency and/or HA.

An embodiment of a method according to the invention comprises that one or more grooves are formed on the upper and/or undersides of the thread flanks, preferably at the central parts of the flanks, which grooves, in the peripheral direction of the thread flanks, extend along all or substantial parts of the longitudinal extent of the implant.

In another embodiment, a groove or grooves are made along the longitudinal extent of the implant with the same or varying width and/or depth and/or position along the extents of the flanks.

By what has been proposed above, the desired solutions to the problems are achieved. The proposals have been found to be feasible through carrying out animal tests which show desired effective formation of new bone in the groove arrangements and show that effective retention principles can be created for the implant even in jaw bones with considerable involvement of soft bone (trabecular bone, marrow, etc).

For purposes of summarizing the invention, certain aspects, advantages and novel features of the invention have been described herein. It is to be understood that not necessarily all such advantages may be achieved in accordance with any particular embodiment of the invention. Thus, the invention may be embodied or carried out in a manner that achieves or optimizes one advantage or group of advantages as taught herein without necessarily achieving other advantages as may be taught or suggested herein.

BRIEF DESCRIPTION OF THE DRAWINGS

Presently proposed embodiments of the device and arrangement according to the invention will be described below with reference to the attached drawings, in which:

FIGS. 8-8b show, in longitudinal section and in a diagrammatic form, reinforcement elements, obtained by bone guidance, for implants.

FIG. 9 shows, in longitudinal section and in a diagrammatic form, the application of bone-growth-stimulating agent.

FIG. 10 shows, in longitudinal section and in a diagrammatic form, another embodiment of reinforcement elements produced with bone guidance.

FIG. 11 is a diagram showing the removal torques in tests carried out on dogs and rabbits.

DETAILED DESCRIPTION OF THE PREFERRED EMBODIMENTS

Figure 1:
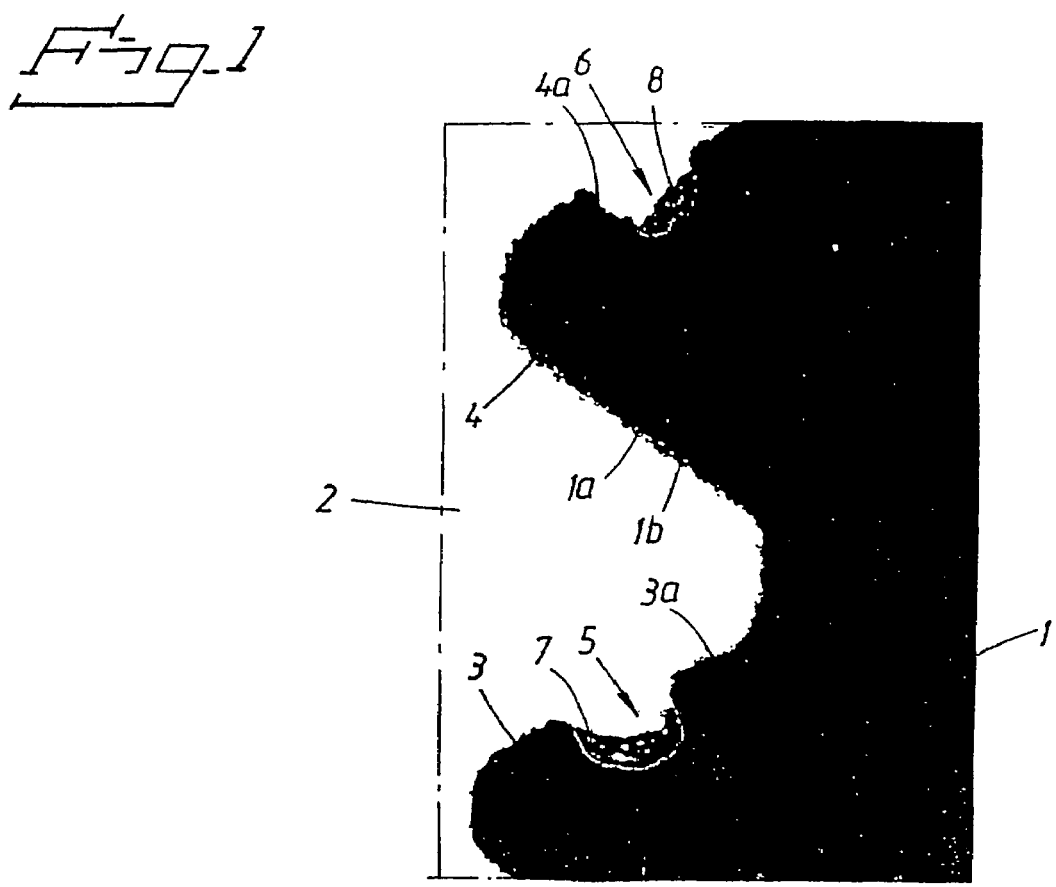
FIG. 1 is a longitudinal section through an implant, showing peripherally extending grooves arranged on the upper sides of the thread flanks, and it will also be seen that new bone has formed and filled the flanks and said grooves.

In FIG. 1, parts of an implant are designated by 1. In said part, the implant is provided with a thread which is exposed to the jaw bone and which, in FIG. 1, is represented with two thread flanks 3 and 4. The thread flanks are provided on their upper sides 3a and 4a with grooves 5 and 6. The surface of the thread or thread flanks which is exposed to the jaw bone 2 is designated by 1a. In this illustrative embodiment, the thread flanks are designed with an oxide layer 1b which is already known from the implants sold by Nobel Biocare AB. The oxide layer is characterized on the one hand by a high pore content and on the other hand by the fact that it stimulates new formation of bone in conjunction with application of the implant in the jaw bone. The surface 1a or the oxide layer 1b can be provided with bone-growth-stimulating agent, for example HA, in the manner specified by the Applicant of the present application in said applications and patents. The type of implant or implant type or implant type can be of the kind called TiUnite, which is a type of oxide layer. Alternatively, bone-growth-stimulating agent in the form of TS of soft consistency can be applied in the grooves 5, 6 before the implant is fitted in the jaw bone (not shown). In FIG. 1, new bone 7,8 has formed in the bottom of the peripheral spiral groove, which in FIG. 1 is represented by 5 and 6. The new-fanned bone is of the cortical type and thus extends from the cortical part (not shown in FIG. 1) of the jaw bone down into the part 2 of the jaw bone which has been assumed to consist of trabecular or marrow-filled bone. The cortical spiral 7, 8 is thus contiguous with the cortical part of the jaw bone and thus arranged to participate in the retention of the implant in the jaw bone in the specific case where the latter has a considerable involvement of soft bone.

Figure 2:
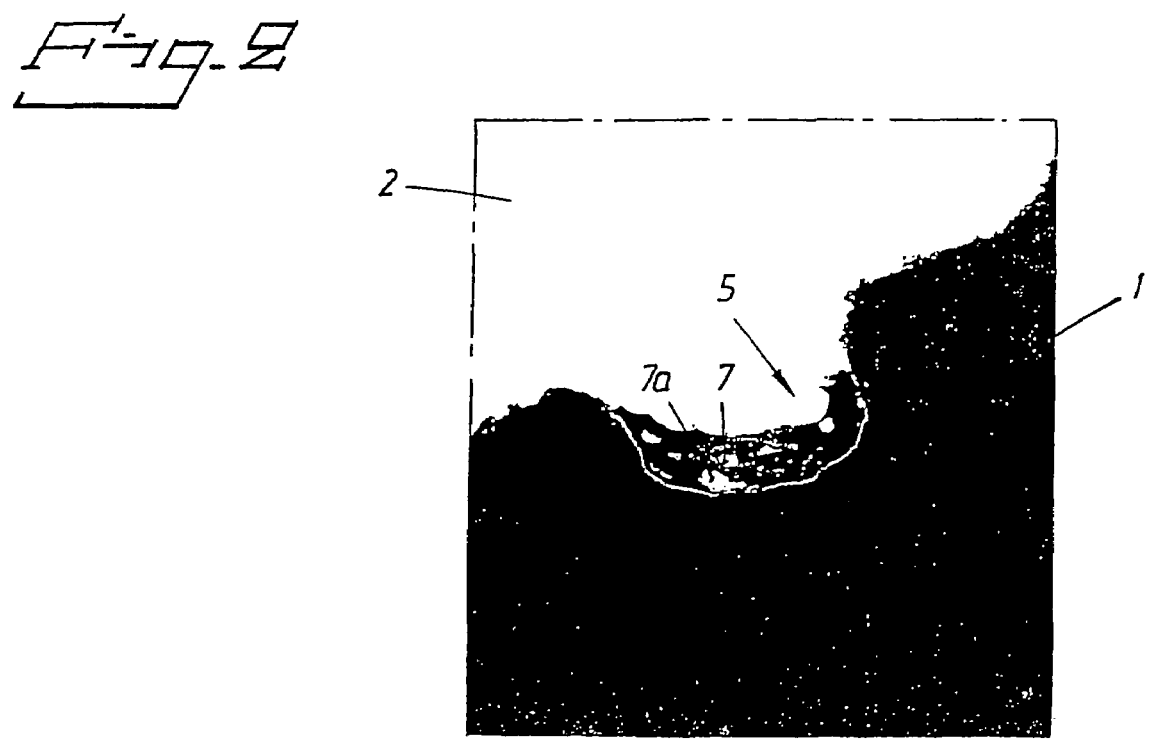
FIG. 2 shows, in an enlarged longitudinal section through the implant, growth of bone in a groove shown in FIG. 1.
Figure 3:
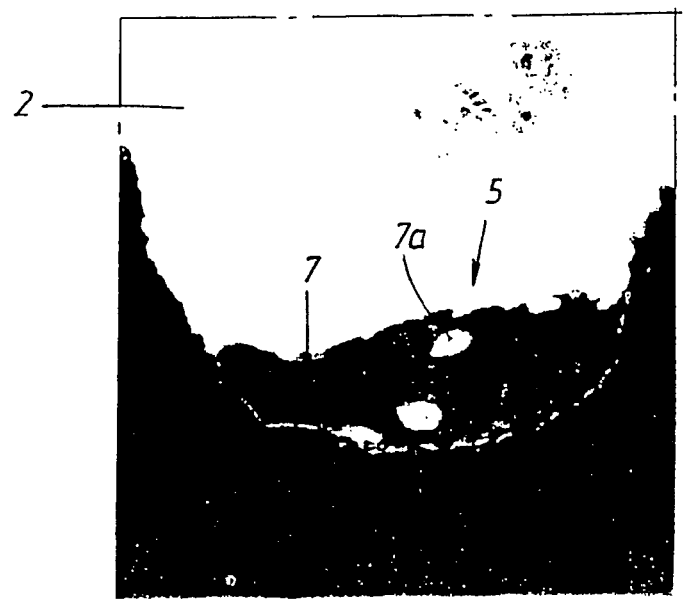
FIG. 3 shows a further enlarged groove according to FIG. 2.

FIGS. 2 and 3 are enlargements showing bone growths 7 and 8 down into the groove 5, 6 (cf. FIG. 1). The downward growth emanates principally from the cortical part of the jaw bone, and the figures also show the enclosed oesyeocytes 7a. The case according to FIGS. 1-3 is comparable to a case with tibia in which the upper sides and undersides of the flanks were studied. 30% of all the threads with grooves showed bone growth, while only 3% of the threads without grooves showed bone growth. Osteogenesis evidently appears to take place in the grooves.

Figure 4:
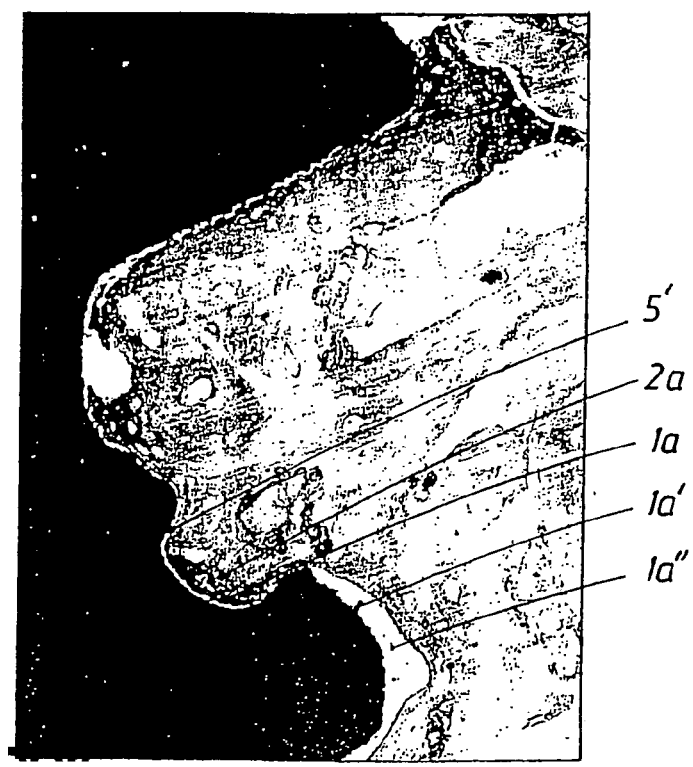
FIG. 4 is a longitudinal section through the implant, showing bone growing down into the groove from surrounding bone.

The case according to FIG. 4 shows new growth 2a of bone which fills out a respective groove 5' in close contact with the implant surface 1a. It will be noted here that there is no contact between bone and implant under the groove 5', i.e., at the implant surface part 1a'. A space or gap 1a" can be present for body fluid.

There is therefore preferential bone growth in the groove, which permits bone guidance and bone formation. The presence of osteocytes indicates that mature bone is present.

Figure 5:
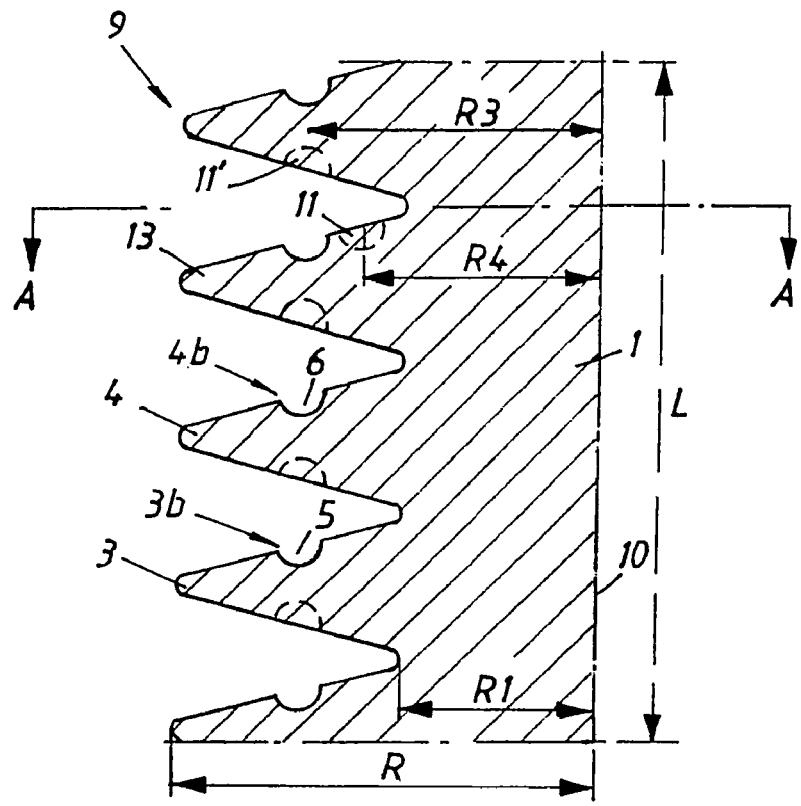
FIG. 5 is a longitudinal section through the implant, showing grooves which are arranged on the thread flanks and which extend in the peripheral direction along the longitudinal direction of the implant.

In accordance with FIG. 5, the implant 1 has a length L which can assume values of known type, and in this connection reference is made to the so-called Branemark system. The implant is arranged with a thread 9 which can extend along all or substantial-parts of the longitudinal extent L of the implant. The thread flanks, for example thread flanks 3 and 4, are arranged with an external diameter R and an internal diameter R1. Said diameters can be constant or can vary along the longitudinal extent L. The recesses on the thread flanks, for example thread flanks 3, 4, comprise grooves which combine to form a spiral groove along the longitudinal extent L of the implant. Groove parts on the thread flanks 3 and 4 are designated by 5 and 6. In accordance with the above, the grooves are arranged on the upper sides of the thread flanks. The groove parts on the thread flanks can be arranged at central parts 3b, 4b of the thread flanks. In one illustrative embodiment, the groove or the groove parts are arranged at a distance R3 from the center axis 10 of the implant. Said distance R3 can be the same for all the groove parts or can vary between the different groove parts. Alternatively or complementarily, the thread flanks can be provided with more than one groove, and an example of such an additional groove has been designated by 11. Alternatively or complementarily, the thread flanks can be provided with grooves 11' on their undersides. The terms upper sides and undersides can also relate to whether the implant is to be applied in the upper jaw or lower jaw.

Figure 6:
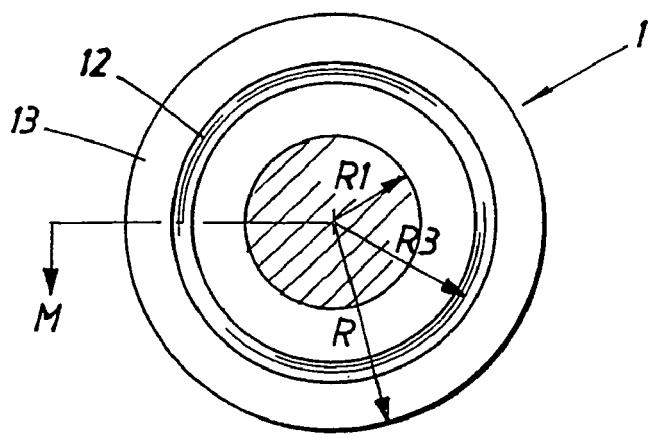
FIG. 6 shows the implant in a cross section A-A from FIG. 5.

FIG. 6 shows how a thread flank groove 12 extends circularly and peripherally around the thread flank 13 (see also FIG. 5) in question. In accordance with the examples below, it has been shown that the degree of anchoring increases considerably by what is proposed according to the invention. Thus, the removal torques M have increased considerably, see below. In the view shown in FIG. 6, the groove 12 can be given a variation for radius R3.

Figure 7:
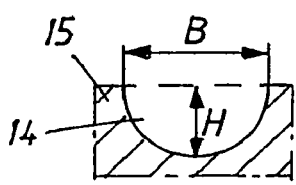
FIG. 7 is a cross section showing an example of the shape of the groove.

FIG. 7 shows a cross section of a groove 14 in a thread flank 15. In this case the width of the groove is indicated by B and the depth of the groove is indicated by H. In the cross section shown according to the embodiment in FIG. 7, the groove has been shown in a semicircle shape. However, the groove can assume other shapes, for example triangular, rectangular or square, or combinations thereof, etc.

FIG. 8 shows a cortical part 16 of a jaw bone which also has a trabecular part 17. An implant 18 with peripheral spiral-shaped groove is shown by 18. In FIG. 8a, the lower parts of the implant 18 have been removed for the sake of clarity. The spiral-shaped 3 groove is shown by 19, which in principle can also represent a reinforcement element for securing the implant. The reinforcement element has arisen through formation of new bone. The parts of the groove or of the reinforcement element at the cortical part 16 permit access for the body fluid generated by the cortical part in the hole formed (pre-formed) in the jaw bone during application of the implant in the inward (downward, upward) extending recess. A reinforcement element consisting of new cortical bone can thus be obtained down (deep down) in the trabecular part of the gum.

FIG. 8b shows that other shapes or extents of the reinforcement element 19' are possible, for example straight or twisted reinforcement elements. The reinforcement element increases the retention of the implant, and the element(s) can be arranged with greater dimensions at their outer parts.

FIG. 9 shows the use of bone-growth-stimulating agent 20 which can have a gel-like consistency and is applied in the spaces 21 between the thread flanks. The agent can stimulate bone growth in the soft parts of the jaw bone over a comparatively long time and contribute to the increased retention function even for a protracted period of time.

FIG. 10 aims to show alternative groove applications for obtaining alternative reinforcing elements, cf FIG. 8b. Thus, recesses 22, 23 and 24 in the thread flanks can be seen to form grooves which extend through the recesses and the spaces 25, 26 between the thread flanks. In a further alternative or complementary embodiment, the implant can be provided with grooves 27 extending in the longitudinal direction of the implant.

FIG. 11 shows examples of the removal torques which were required on the implant applied on rabbits and dogs in accordance with the principles of the invention. The case with rabbits is indicated by 28 and 29 and the case with dogs is indicated by 30, 31 and 32.

In the case with rabbits (9 rabbits were used), implants S1 and S3 were used in a bone (femur and tibia) and a control implant in another bone. The time of incorporation was 6 weeks. The implants had TiUnite,(oxide layer), surfaces. The groove widths were 110 (S1) and 200 (S3) μm and the groove depth was 70 μm. The following removal torques were obtained:

ST: mean value for femur 63 Ncm
C: mean value for femur 51 Ncm
S1: mean value for tibia 37 Ncm
C: mean value for tibia 30 Ncm
(S1−C)/C=0.27 femur
(S1−C)/C=0.30 tibia
S3: mean value for femur 63 Ncm
C: mean value for femur 59 Ncm
S3: mean value for tibia 35 Ncm
C: mean value for tibia 32 Ncm
(S3−C)/C=0.8 femur
(S3−C)/C=0.08 tibia where SX−C is the mean value of the sum taken from each pair from each rabbit.

In the case with dogs, the following values were obtained in the same way with groove widths 80 (SO), 110 (Si) and 160 (S2):

SO: mean value 150 Ncm
S1: mean value 119 Ncm
S2: mean value 99 Ncm
C: mean value 102 Ncm
(SO−C)/=0.21

(S1−C)/C=0.17
(S2−C)/C=0.07 where SX−C is the mean value of the sum taken from each pair from each dog.

The increase in area can be established at ca. 10%.

The implant as such can be made of tissue-compatible material, for example titanium.

Although the foregoing systems and methods have been described in terms of certain preferred embodiments, other embodiments will be apparent to those of ordinary skill in the art from the disclosure herein. Additionally, other combinations, omissions, substitutions and modifications will be apparent to the skilled artisan in view of the disclosure herein. While certain embodiments of the inventions have been described, these embodiments have been presented by way of example only, and are not intended to limit the scope of the inventions. Indeed, the invention is not limited to the embodiments shown above by way of example, and instead it can be modified within the scope of the attached patent claims and the inventive concept.

What is claimed is:

1. A dental implant, comprising a body portion that includes a thread, the thread having a first extent in a longitudinal direction of the dental implant and comprising a thread flank having an upper side between an outer periphery and an upper, inner periphery of the thread flank, and a lower side between a lower, inner periphery and the outer periphery of the thread flank, wherein, along at least a portion of the first extent of the thread, the thread flank includes at least one helical groove that has a lowest point with respect to an outer surface of the thread flank, the lowest point of the at least one helical groove being disposed on the thread flank between the upper, inner periphery and the lower, inner periphery of the thread flank, wherein the at least one groove is on the lower side of the thread flank between the lower, inner, periphery and the outer periphery.

2. The dental implant of claim 1, wherein the at least one groove extends along substantially the entire portion of the first extent.

3. The dental implant of claim 1, wherein the dental implant includes a plurality of grooves that are between the inner and outer peripheries of the thread flank.

4. The dental implant of claim 1, wherein the at least one groove is configured to be placed opposite at least a cortical part of the jaw bone for attachment and new formation of bone from said cortical part.

5. The dental implant of claim 1, wherein the at least one groove is configured to increase a surface area of the thread flank exposed to the jaw bone by 5-15%.

6. The dental implant of claim 1, wherein the at least one groove has a groove depth and groove width that are substantially the same along the first extent.

7. The dental implant of claim 1, wherein the at least one groove has a groove depth or groove width that varies along the first extent.

8. The dental implant of claim 1, wherein, over the first extent, at least one groove is situated at a substantially constant distance along the flank with respect to a center axis of the implant.

9. The dental implant of claim 1, wherein over the first extent the at least one groove is situated at a varying distance along the thread flank with respect to a center axis of the implant.

10. The dental implant of claim 1, wherein outer surfaces of the thread flank are provided with porous layers.

11. The dental implant of claim 1, wherein outer surfaces of the thread flank are provided with oxidation layers.

12. The dental implant of claim 1, wherein the thread flank are provided with bone-growth-stimulating agents.

13. The dental implant of claim 1, wherein the bone-growth-stimulating agents are applied in the at least one groove.

14. The dental implant of claim 1, wherein the at least one groove has a width that is in the range of 50-300 μm.

15. The dental implant of claim 1, wherein the at least one groove has a depth (H) that is in the range of 50-100 μm.

16. A dental implant, comprising a body portion that includes a thread, the thread having a first extent in a longitudinal direction of the dental implant and comprising a thread flank having an upper side between an outer periphery and an upper, inner periphery of the thread flank, and a lower side between a lower, inner periphery and the outer periphery of the thread flank, wherein, along at least a portion of the first extent of the thread, the thread flank includes at least one helical groove that has a lowest point with respect to an outer surface of the thread flank, the lowest point of the at least one helical groove being disposed on the thread flank between the upper, inner periphery and the lower, inner periphery of the thread flank, wherein the at least one groove is positioned on a central part of the thread flank between the inner and outer peripheries.

17. A dental implant, comprising a body portion that includes a thread, the thread having a first extent in a longitudinal direction of the dental implant and comprising a thread flank having an upper side between an outer periphery and an upper, inner periphery of the thread flank, and a lower side between a lower inner periphery and the outer periphery of the thread flank, wherein, along at least a portion of the first extent of the thread, the thread flank includes at least one helical groove that has a lowest point with respect to an outer surface of the thread flank, the lowest point of the at least one helical groove being disposed on the thread flank between the upper, inner periphery, and the lower, inner periphery of the thread flank, wherein the at least one groove is on an upper side of the thread flank.

18. The dental implant of claim 17, wherein the at least one groove extends along Substantially the entire portion of the first extent.

19. The dental implant of claim 17, wherein the dental implant includes a plurality of grooves that are between the inner and outer peripheries of the thread flank.

20. The dental implant of claim 17, wherein the at least one groove is configured to increase a surface area of the thread flank exposed to the jaw bone by 5-15%.

21. The dental implant of claim 17, wherein the at least one groove has a groove depth and groove width that are substantially the same along the first extent.

22. The dental implant of claim 17, wherein the at least one groove has a groove depth or groove width that varies along the first extent.

23. The dental implant of claim 17, wherein, over the first extent, at least one groove is situated at a substantially constant distance along the flank with respect to a center axis of the implant.

24. The dental implant of claim 17, wherein over the first extent the at least one groove is situated at a varying distance along the thread flank with respect to a center axis of the implant.

25. The dental implant of claim 17, wherein outer surfaces of the thread flank are provided with porous layers.

26. The dental implant of claim 17, wherein outer surfaces of the thread flank are provided with oxidation layers.

27. The dental implant of claim 17, wherein the thread flank are provided with bone-growth-stimulating agents.

28. The dental implant of claim 17, wherein the bone-growth-stimulating agents are applied in the at least one groove.

29. The dental implant of claim 17, wherein the at least one groove has a width that is in the range of 50-300 μm.

30. The dental implant of claim 17, wherein the at least one groove has a depth (H) that is in the range of 50-100 μm.

31. A method for producing a dental implant, the method comprising: providing a body portion having a thread configured to be exposed to a jawbone, the thread having a first extent longitudinal direction of the implant, the thread having a thread flank with an upper side that extends between an upper inner, upper periphery to an outer periphery and a lower side that extends between an inner, lower periphery of the thread to the outer periphery; and forming at least one helical groove on the thread flank, the at least one groove having a lowest point positioned on the thread flanks between the inner, upper periphery and the inner, lower periphery of the tread, wherein the at least one groove is formed on the upper side of the thread flank.

32. The method of claim 31, comprising forming, along the first extent, the least one groove with a varying width.

33. The method of claim 31, comprising forming, along the first extent, the least one groove with a varying depth.

34. The method of claim 31, comprising forming, along the first extent, the least one groove with a varying position between the inner and outer peripheries.

35. A method for producing a dental implant, the method comprising: providing a body portion having a thread configured to be exposed to a jawbone, the thread having a first extent longitudinal direction of the implant, the thread having a thread flank with an upper side that extends between an upper inner, upper periphery to an outer periphery and a lower side that extends between an inner, lower periphery of the thread to the outer periphery; and forming at least one helical groove on the thread flank, the at least one groove having a lowest point positioned on the thread flanks between the inner, upper periphery, and the inner, lower periphery of the thread, wherein the at least one groove is formed on the lower side of the thread flank.

36. The method of claim 35, comprising forming, along the first extent, the least one groove with a varying width.

37. The method of claim 35, comprising forming, along the first extent, the least one groove with a varying depth.

38. The method of claim 35, comprising forming, along the first extent, the least one groove with a varying position between the inner and outer peripheries.

39. A method for producing a dental implant, the method comprising: providing a body portion having a thread configured to be exposed to a jawbone, the thread having a first extent longitudinal direction of the implant, the thread having a thread flank with an upper side that extends between an upper inner, upper periphery to an outer periphery and a lower side that extends between an inner, lower periphery of the thread to the outer periphery; and forming at least one helical groove on the thread flank, the at least one groove having a lowest point positioned on the thread flanks between the inner, upper periphery and the inner, lower periphery of the thread wherein the at least one groove is formed on a central part of the thread flank between the inner and outer peripheries.

* * * * *

UNITED STATES PATENT AND TRADEMARK OFFICE
CERTIFICATE OF CORRECTION

PATENT NO. : 7,281,925 B2
APPLICATION NO. : 11/169189
DATED : October 16, 2007
INVENTOR(S) : Jan Hall It is certified that error appears in the above-identified patent and that said Letters Patent is hereby corrected as shown below:

In Column 1, line 2, above "This" insert -- PRIORITY INFORMATION -- (As a heading).

In Column 3, line 61, delete "7,8" and insert -- 7, 8--, therefore.

In Column 3, line 63, delete "fanned" and insert -- formed --, therefore.

In Column 4, line 7, delete "oesyeocytes" and insert -- osteocytes --, therefore.

In Column 4, line 27, delete "substantial-parts" and insert -- substantial parts --, therefore.

In Column 5, line 26, delete "cf" and insert -- cf. --, therefore.

In Column 5, line 41, delete "TiUnite,(oxide" and insert -- TiUnite, (oxide --, therefore.

In Column 7, line 32, in Claim 17, before "inner" delete "lower" and insert -- lower, --, therefore.

In Column 7, line 38, in Claim 17, delete "periphery," and insert -- periphery --, therefore.

In Column 7, line 42, in Claim 18, delete "Substantially" and insert -- thread --, therefore.

UNITED STATES PATENT AND TRADEMARK OFFICE
CERTIFICATE OF CORRECTION

| | |
|---|---|
| PATENT NO. | : 7,281,925 B2 |
| APPLICATION NO. | : 11/169189 |
| DATED | : October 16, 2007 |
| INVENTOR(S) | : Jan Hall |

It is certified that error appears in the above-identified patent and that said Letters Patent is hereby corrected as shown below:

In Column 8, line 21, in Claim 31, delete "tread" and insert -- thread --, therefore.

In Column 8, line 41, in Claim 35, delete "periphery," and insert -- periphery --, therefore.

Signed and Sealed this

Sixth Day of May, 2008

JON W. DUDAS
*Director of the United States Patent and Trademark Office*